United States Patent [19]

Bassi et al.

[11] Patent Number: 5,780,013
[45] Date of Patent: Jul. 14, 1998

[54] GLIADIN-CONTAINING HAIRSPRAY

[75] Inventors: Sukh Bassi, Atchison, Kans.; Larry Murphy, Richardson, Tex.; Clodualdo C. Maningat, Platte City; Li Nie, Kansas City, both of Mo.

[73] Assignee: Midwest Grain Products, Atchison, Kans.

[21] Appl. No.: 738,094

[22] Filed: Oct. 25, 1996

[51] Int. Cl.⁶ .......................................... A61K 7/11
[52] U.S. Cl. .................. 424/45; 424/78.02; 424/70.11; 424/47; 424/DIG. 1; 424/DIG. 2; 514/2
[58] Field of Search ................ 424/47, DIG. 1, 424/DIG. 2, 78.02, 70.11; 514/2, 957

[56] References Cited

U.S. PATENT DOCUMENTS

| | | | |
|---|---|---|---|
| 4,195,077 | 3/1980 | Marsh et al. | 424/70.11 |
| 4,518,614 | 5/1985 | Parkinson | 514/2 |
| 4,897,262 | 1/1990 | Nandagiri et al. | 424/70.11 |
| 5,021,238 | 6/1991 | Martino et al. | 424/DIG. 2 |
| 5,094,838 | 3/1992 | Benson et al. | 424/DIG. 1 |
| 5,126,126 | 6/1992 | Varaprath et al. | 424/47 |
| 5,176,898 | 1/1993 | Goldberg et al. | 424/47 |
| 5,614,173 | 3/1997 | Ulmer et al. | 424/47 |

FOREIGN PATENT DOCUMENTS 1122076   7/1968   United Kingdom.

OTHER PUBLICATIONS

Martino, G. T et al. (1992). Spray Technology & Marketing, Mar. Issue, pp. 34–39.

Johnsen, M. A. (1992). Spray Technology & Marketing, Jun. Issue, pp. 32–40.

*Primary Examiner*—Raj Bawa
*Attorney, Agent, or Firm*—Hovey, Williams, Timmons & Collins

[57] ABSTRACT

Improved aqueous gliadin-containing hairspray formulations are provided which include form about 0.5–10% by weight gliadin dispersed in an aqueous alcohol-containing solvent system at a pH of from about 3–5.5. The preferred formulations have a VOC content of up to about 55% and contain little or no synthetic polymer.

10 Claims, No Drawings

GLIADIN-CONTAINING HAIRSPRAY

BACKGROUND OF THE INVENTION

1. Field of the Invention

The present invention is broadly concerned with improved hairspray formulations which contain gliadin as a naturally occurring protein polymer and which have low volatile organic compound (VOC) levels. More particularly, the invention pertains to such formulations wherein gliadin is dispersed in an aqueous, alcohol-containing solvent system at a relatively low pH of from about 3–5.5.

2. Description of the Prior Art

Hairsprays have long been provided as a grooming aid for hairstyling and maintenance purposes. These formulations have been placed in pressurized containers with propellants, or in non-pressurized bottles equipped with simple pump sprayers. Generally, prior hairspray formulations have included significant amounts of synthetic polymers such as polymethylmethacrylate or other acrylic acid-based polymers, vinylmethyl ethers, maleic anhydride or polyvinyl pyrrolidone.

In recent years, environmental concerns have led to the enactment of increasingly stringent VOC standards for hairsprays and other like products. Indeed, the State of California is presently proposing that these products have a maximum VOC content of 55%. At the same time, many consumers have expressed a strong preference for products either devoid of or using only a minimum of synthetic resins; rather, these consumers prefer "all natural" products where possible.

Gliadin is a single-chained protein having an average molecular weight of about 30,000–40,000, with an isoelectric point at pH 4.0–5.0. Gliadin can be obtained by fractionation of wheat gluten and is considered to be a premium product. Gliadin is known to improve the freeze thaw stability of frozen doughs and also improve microwave stability. The product may also be used as a chewing gum base replacer, a pharmaceutical binder, and to improve the texture and mouth feel of pasta products; although gliadin has also been used in certain cosmetic products, it has never found utility in hairsprays or similar compositions.

SUMMARY OF THE INVENTION

The present invention is predicated upon the discovery that very low VOC hairspray formulations can be provided which include gliadin as the principal polymer therein, thus achieving the twin goals of an environmentally friendly product which has little or no synthetic polymer content. Broadly speaking, the hairspray formulations of the invention comprise from about 0.05–10% by weight gliadin dispersed in an aqueous, alcohol-containing solvent system, the formulation having a pH of from about 3.0–5.5. Such formulations have been found to give good hair control without undue discoloration or other undesirable properties. At the same time, the formulations can be prepared with low VOC contents on the order of up to about 85%, and more preferably up to about 55%.

In preferred forms, the formulations include from about 3–7% by weight gliadin and are dispersed within a solvent system making up from about 90–98% by weight of the formulation. The solvent system comprises (and advantageously consisting essentially of) water, alcohol, and acid, such that the water content of the formulation is from about 20–75% by weight (more preferably from about 30–50% by weight) while the alcohol content is from about 20–92% by weight (more preferably from about 30–60% by weight) and the acid is present at a minor level of from about 0.5–3% by weight of the formulation. The presently preferred formulation contains less than 55% by weight alcohol, without alcohol being the only volatile organic compound present; therefore, the VOC content of the formulation is below the most stringent environmental standards now proposed.

The low pH levels of the hairspray formulations are achieved by presence of acid. A variety of acids can be used, with malic acid being the most preferred. Use of this acid insures that the formulation leaves a clearer film on hair.

A number of optional ingredients can also be used in the formulations, such as plasticizer(s), conditioning agent(s), perfumes, moisturizers (e.g., panthenol), silicone, sunscreens, and anti-static agents. Generally, these additives are used in minor amounts.

DETAILED DESCRIPTION OF THE PREFERRED EMBODIMENT

A preferred hairspray formula in accordance with the invention was prepared and contained 53.49% by weight denatured ethanol (95% ethanol 39A), 3.89% by weight purified gliadin, 41.2% by weight purified water and 1.42% by weight malic acid. The composition was prepared by first sprinkling the gliadin (obtained by the gliadin extraction process described in pending application for U.S. Pat. No. 08/526,078, filed Sep. 11, 1995 and incorporated by reference herein) into the ethanol using a strong impeller agitation until a milky solution was obtained. The water was next slowly added with continued strong agitation. At this point, the pH of the solution was adjusted with the malic acid to a level of about 3.5–3.8. This composition is especially suited for use with a non-pressurized pump spray container. The hairspray formula has a very low VOC content and meets the most stringent of presently proposed environmental standards for such products. At the same time, the formulation completely avoids the use of typical synthetic polymers used in prior hairspray compositions.

While the foregoing formula is presently preferred, a number of variations may be made without departing from the principles of the invention. For example, other solvents can be used in place of at least some of the alcohol, e.g., ethoxydiglycol. The principal issue in the use of such additional solvents is that of maintaining the gliadin in dispersion during extended storage and use. While ethanol is the most preferred alcohol because of its cost and physical properties, other alcohols could be used, most notably isopropanol.

The use of acid in the formulation serves primarily to give a clearer film upon application to hair. While malic acid is preferred, a number of $C_2$–$C_{10}$ mono- or polyhydroxy acids could be employed, such as lactic, tartaric or glycolic acids. The acids would generally be present at levels to achieve a final composition pH of from about 3–5.5 and more preferably from about 3.5–4.0.

Optional ingredients could also be provided in formulations of the invention, e.g., plasticizers, conditioning agents and anti-static agents. The plasticizers would be used to give the hairspray formulation more flexibility as applied to the hair for better hair control. In addition, plasticizers may be used to control flaking or whitening of the composition on the hair. Exemplary plasticizers usable in the context of the invention would include diethyl phthalate, triethylcitrate, and would normally be present at a level of up to about 2% by weight, and more preferably from about 0.01–0.5% by weight.

Conditioning agents would typically be used to increase gloss characteristics on hair. Conditioning agents such as esters (e.g., lactic esters and isopropyl myristate) or polyalkylene glycols (e.g., polyethylene glycols having a molecular weight of from about 180–900) would be suitable for this purpose.

Some aqueous hairspray formulations tend to generate static electric charge in the hair and an appropriate anti-static agent could be added to counteract this effect. Quaternary compounds (e.g., stearalkonium chloride, cetyl pyridinium) could be used for this purpose, typically in minor amounts of up to about 2.5% by weight.

The following table summarizes broad and preferred ranges for the components of hairspray formulations in accordance with the invention.

| Ingredient | Broad Range % By Weight | Preferred Range % By Weight |
|---|---|---|
| Gliadin | 0.5–10 | 3–7 |
| Total Solvent System[1] | 90–98 | 94–97 |
| Alcohol | 20–92 | 30–60 |
| Water | 20–75 | 30–50 |
| Acid | to pH 3.0–5.5 | to pH 3.5–4.0 |
| Plasticizer(s)* | up to 2% | up to about 0.5% |
| Conditioning Agent(s)* | up to 1% | up to about 0.5% |
| Anti-Static Agent(s)* | up to 0.5% | up to about 0.2% |

[1]Total solvent system comprises water, alcohol, acid and additional non-aqueous solvents, if any.
*Preferred optional ingredients

We claim:

1. An aqueous, low VOC hairspray formulation comprising from about 0.05–10% by weight gliadin dispersed in an aqueous, alcohol-containing solvent system, the formulation having a pH of from about 3.0–5.5 adjusted by the addition of an acid to said formulation, said gliadin having a molecular weight of from about 30,000–40,000, said formulation comprising from about 20–75% by weight water and from about 20–92% by weight of a lower alcohol, said formulation having a VOC content of up to about 85%.

2. The formulation of claim 1, said gliadin being present at a level of from about 3–7% by weight.

3. The formulation of claim 1, said alcohol being present at a level of from about 20–85% by weight of the formulation.

4. The formulation of claim 3, said water being present at a level of from about 30–50% by weight, and said alcohol being present at a level of from about 30–60% by weight.

5. The formulation of claim 1, said alcohol being selected from the group consisting of ethanol and isopropanol.

6. The formulation of claim 1, said pH being from about 3.5–4.

7. The formulation of claim 1, said acid selected from the group consisting of the $C_2$–$C_{10}$ mono- or polyhydroxy acids.

8. The formulation of claim 7, said acid being malic acid.

9. The formulation of claim 1, said formulation including optional ingredients selected from the group consisting of plasticizers, conditioning agents and anti-static agents.

10. The formulation of claim 11, said VOC content being up to about 55%.

* * * * *